US00PP19988P3

(12) United States Plant Patent
Dirr

(10) Patent No.: US PP19,988 P3
(45) Date of Patent: May 12, 2009

(54) ***GARDENIA* PLANT NAMED 'MADGA I'**

(50) Latin Name: *Gardenia augusta*
Varietal Denomination: Gardenia MADGA I

(75) Inventor: Michael A. Dirr, Bogart, GA (US)

(73) Assignee: University of Georgia Research Foundation, Athens, GA (US)

( * ) Notice: Subject to any disclaimer, the term of this patent is extended or adjusted under 35 U.S.C. 154(b) by 70 days.

(21) Appl. No.: 11/894,426

(22) Filed: Aug. 21, 2007

(65) Prior Publication Data

US 2009/0055982 P1 Feb. 26, 2009

(51) Int. Cl.
*A01H 5/00* (2006.01)

(52) U.S. Cl. ..... Plt./255
(58) Field of Classification Search ..... Plt./255
See application file for complete search history.

(56) References Cited

U.S. PATENT DOCUMENTS

| | | | | |
|---|---|---|---|---|
| PP364 | P | * | 2/1940 | Wright |
| PP8,755 | P | | 5/1994 | Hayes et al. |
| PP8,887 | P | | 9/1994 | Cook |
| PP15,189 | P3 | | 9/2004 | Barendse |

* cited by examiner

*Primary Examiner*—Wendy C. Haas
(74) *Attorney, Agent, or Firm*—Davis Wright Tremaine LLP

(57) ABSTRACT

A new and distinct cultivar of common *gardenia*, *Gardenia augusta,* which is characterized by a unique upright columnar dense growth habit; small lustrous black green foliage that holds the color in winter, increased cold hardiness (Zone 6) compared to Zone 8 for the typical species variety; abundant, fragrant, white flowers in May–June with repeat blooming into August–September and colorful six-winged orange-red, 2.5 cm long fruits maturing in October and persisting into December.

3 Drawing Sheets

Figure 1:
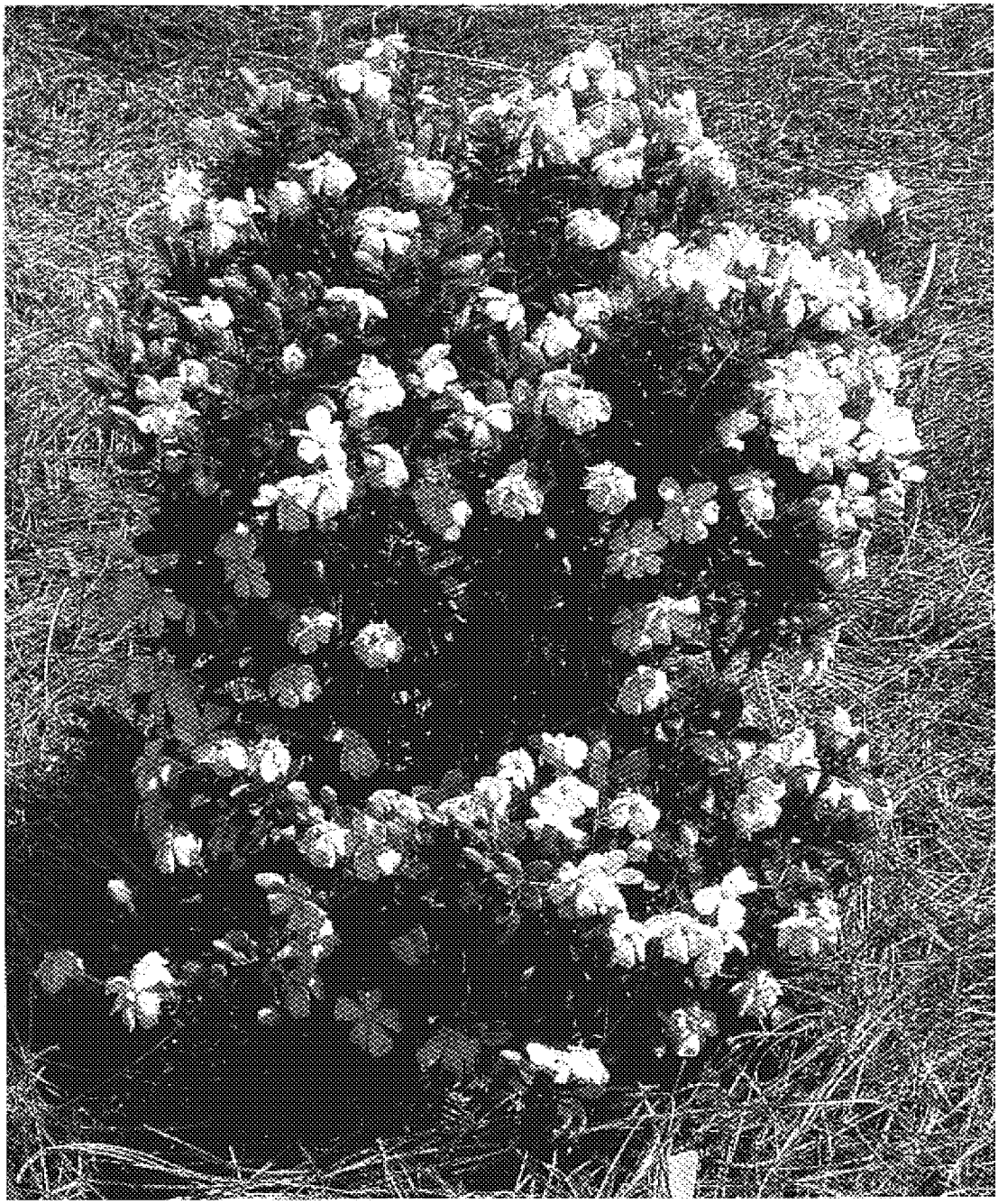

Botanical Classification: *Gardenia augusta.*
Varietal Denomination: *Gardenia* 'MADGA I'.

BACKGROUND OF THE INVENTION

The present invention relates to a new and distinct cultivar of the ornamental flowering shrub *Gardenia augusta,* known as common *gardenia* and hereafter referred to by the varietal denomination 'MADGA I'. It can be used in containers, for small hedges, and for grouping or accent plants in the border.

The new *gardenia* was selected from seedlings grown from seed collected in 1999 from 'Shooting Star' (unpatented). 'Shooting Star', a selection made by the inventor at Athens, Ga. from seed of *Gardenia augusta* provided in 1983 from the coldest parts of China, is an upright form with large, six-petaled white fragrant flowers suffering little winter damage. 'Shooting Star' did not suffer winter discoloration or dieback in 18 years in Athens, Ga., and in laboratory cold hardiness tests the stems survived −11° F. Typical *Gardenia augusta* is rated USDA Zone 8 (10° to 20° F.).

Five superior seedlings from 'Shooting Star' were selected at Dearing, Ga. in 2000 with different habit, foliage and floral traits. After further evaluation for six years, one selection, 'SS-05-03' has proved remarkably cold tolerant and floriferous, with attractive orange red fruits, small, lustrous black green leaves and a unique upright columnar dense growth habit, and has been named 'MADGA I'.

Asexual reproduction by traditional vegetative cuttings since 2000 in Athens, Ga. has shown that the unique characteristics of this new *gardenia* are stable and reproduced true-to-type in successive generations.

SUMMARY OF THE INVENTION

Plants of the cultivar 'MADGA I' have not been observed under all possible environmental conditions. The phenotype may vary somewhat with variations in environment such as light intensity, temperature and cultural conditions, without any variance in genotype.

The following characteristics have been consistently observed and, to the best knowledge of the inventor, their combination form the unique characteristics of 'MADGA I' as a new and distinct cultivar:

1. Unique, extremely dense columnar growth habit.
2. Excellent cold hardiness, down to USDA Zone 6 (0 to −10° F.).
3. Small lustrous black green leaves which maintain their color and appearance year round.
4. Extremely floriferous with single, six-petaled, white fragrant flowers.
5. Attractive orange red fruits maturing in the fall and persisting into winter.

Plants of 'MADGA I' have been compared, in containers and in the ground, with its parent 'Shooting Star', and with other single flowered varieties such as 'Daruma' (unpatented), 'Grif's Select' (unpatented), 'Kleim's Hardy' (unpatented), 'White Gem' (unpatented) and 'Lynn Lowrey' (unpatented). 'MADGA I' differed from all these varieties in the following characteristics:

1. Compact, upright columnar dense growth habit, with leaves and stems densely produced so the plant almost appears pruned to the columnar shape, compared with the spreading habits of the other varieties.

2. Extremely floriferous. In June 2004, 700 flowers were counted on the original plant, which appeared to be covered in snow. It also reblooms intermittently into August–September, compared to the May–June flowering period of the other varieties.
3. Extensive production of winged, orange-red fruits in the fall, persisting into winter.
4. Small ovate to obovate black green leaves compared to the larger ovate to broad-ovate leaves of the other varieties.

'MADGA I' has similar cold hardiness to 'Shooting Star' and 'Grif's Select', but is more cold hardy than other varieties.

BRIEF DESCRIPTION OF PHOTOGRAPHS

FIG. 1. A 3-year old plant showing habit and floriferous character, taken in late May.

Figure 2:
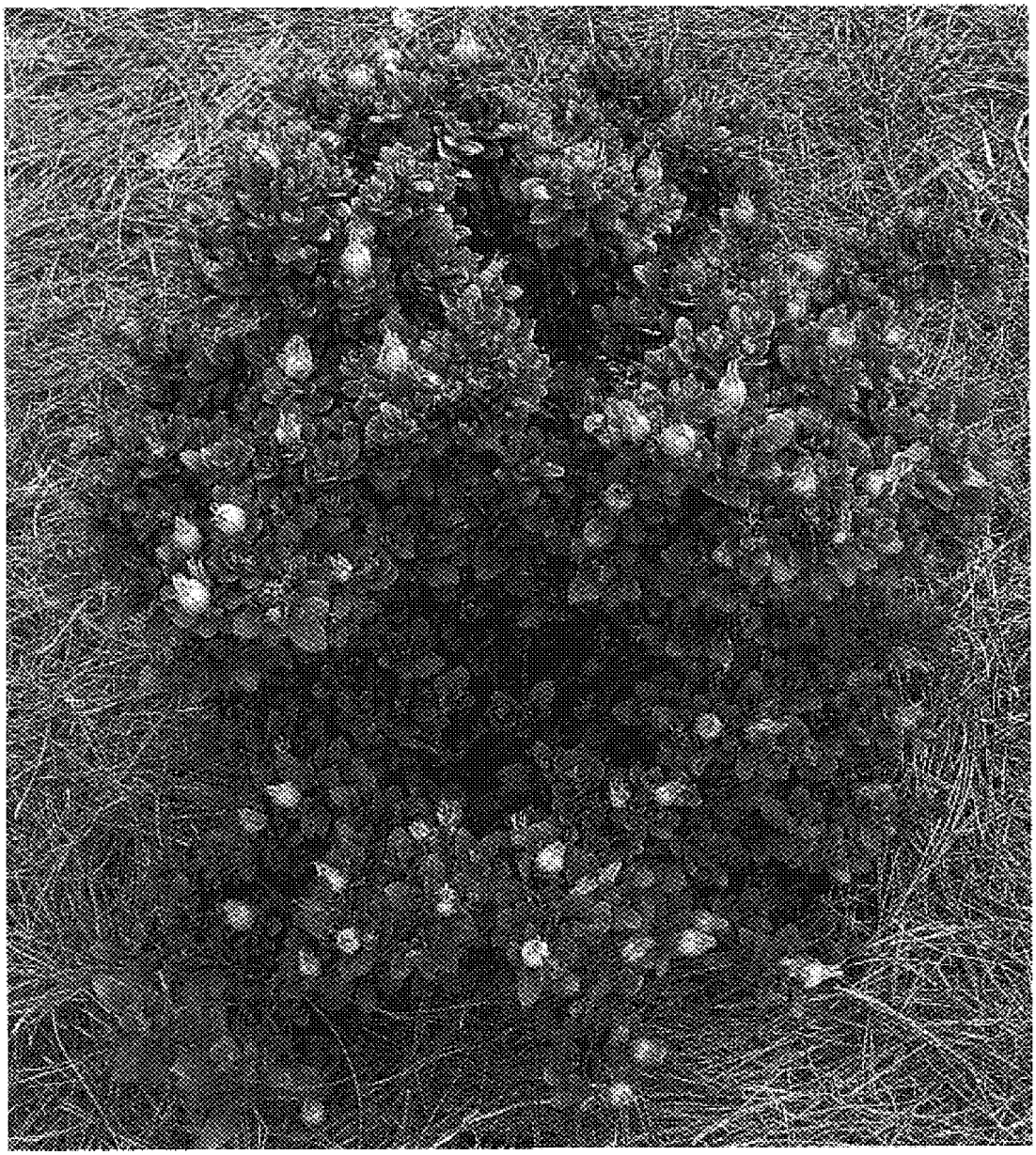

FIG. 2. The same plant showing the dense structure and fruits, taken in early November.

Figure 3:
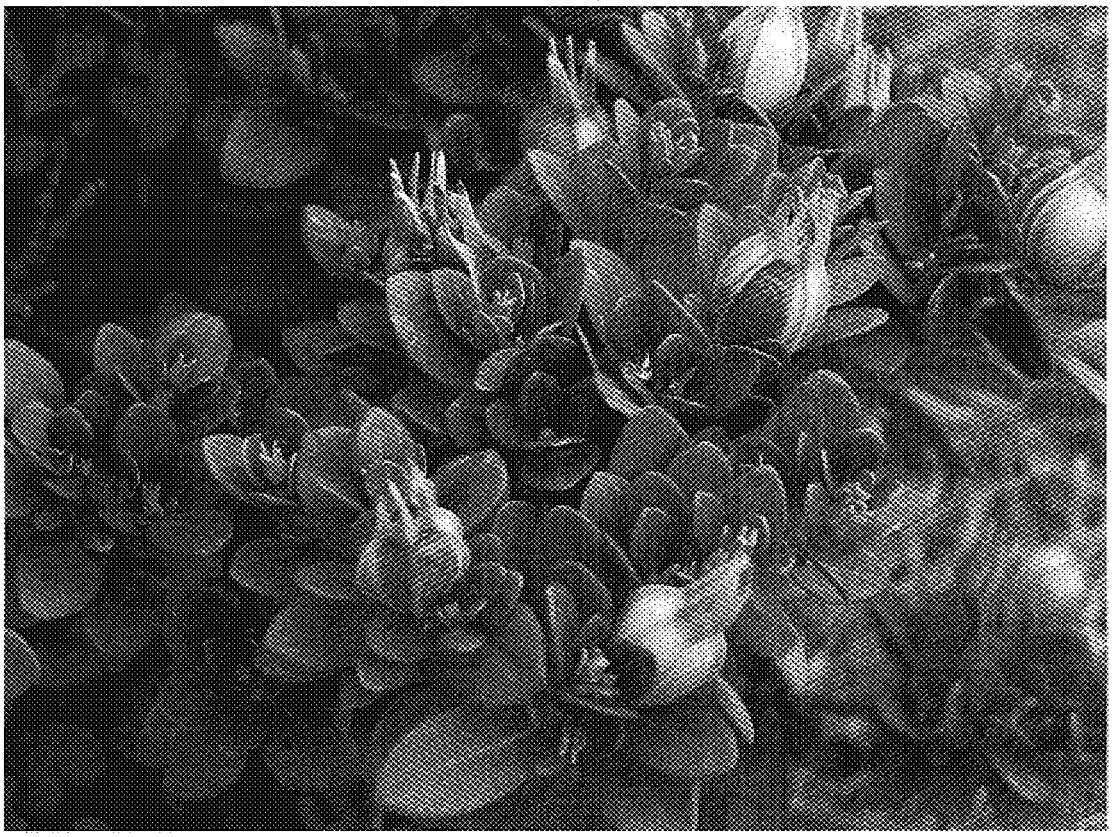

FIG. 3. A close up showing the fruit and leaves, taken in early November.

BOTANICAL DESCRIPTION OF THE PLANT

Unless stated otherwise, the botanical description of 'MADGA I' is based on three-year old plants, growing in 3 gallon containers in an outside nursery research facility in Dearing, Ga. (USDA Zone 7b) under conditions which closely approximate commercial production. Measurements are based on the average of 10 to 20 samples, and were taken throughout the main growth period, from April through September. Colors are based on The Royal Horticultural Society Chart, 2001 edition.

Plant

The plant has an upright, columnar dense growth habit with fine texture of branching. A 3-year old container-grown plant, at Athens, Ga. is 23 cm in height and 16 cm in width.

Stems

Current year stems are round, 2 mm in diameter, finely hairy, with average internode length of 17 mm. They are Yellow-Green 144A in color, and there is no exfoliation. Second year stems are up to 4 mm in diameter, scaly, and Brown 200C in color.

Vegetative Buds

The vegetative buds are opposite in arrangement, single-scaled, conical in shape, 4 mm in length and 1 mm in width, with no pubescence, and the bud scale is Yellow-Green 144A in color.

Leaf

The mature leaf, measured in the middle section of current year stems, averages 28 mm in length and 15 mm in width. The leaf is ovate to obovate, with an abrupt to obtuse apex, cuneate base and entire, revolute margin. The emerging leaf is Yellow-Green 144A on the upper surface and Yellow-Green 144C on the lower surface. In summer, the upper surface is Green 139A and the lower surface is Green 138B. The leaves are arranged opposite on the stem, are thick, almost 1 mm, and are very leathery and waxy. The venation is pinnate with 6 to 7 vein pairs impressed on the lower surface and the vein color is Yellow-Green 144A. The petiole is 1 mm in length and 2 mm in diameter, somewhat oval in cross-section shape with few fine hairs and Yellow-Green 144A in color.

Flower Buds

The flower buds are 38 mm in length and 9 mm in width, oval in shape with no pubescence, and are Yellow-Green 144A in color.

Inflorescence

The inflorescence is a solitary flower, 6.0 cm by 6.0 cm, and a 3-year old plant carries several hundred flowers. The color at emergence and in full bloom is White 155D to pure white, fading to Yellow 11B to Greyed-Orange 165B. The flower is extremely fragrant. The pedicel is Yellow-Green 144A in color, with fine hairs at the base.

The petals, six per flower, average 28 mm in length by 22 mm in width, are obovate in shape with an abrupt to rounded apex, cuneate base and entire margin. There is no pubescence and the texture is smooth and silky. The color of both upper and lower surfaces at peak of bloom is White 155D to pure white.

The pedicel averages 35 mm in length, with no pubescence and is Yellow-Green 144D in color.

The most prolific flowering period is May–June, with intermittent flowering continuing until September.

There are six stamens. The anthers are 16 mm long by one mm wide, and Grey-Brown N199C in color.

There is no separate filament structure.

The pollen is Yellow 13B in color.

The superior pistil is 55 mm in length by five mm in width.

The stigma is obovate in shape, with no pubescence and Yellow-Green 10C in color.

The style is 35 mm in length, tubular in shape, and Yellow 11D in color, with no pubescence. The ovary is 20 mm long, oval in shape, and contains many small (0.3 mm) ovules, Greyed-Yellow 160B in color.

Fruit

The mature fruit is an oval six-valved (winged) berry, measuring 25 to 30 mm in length and 15 to 20 mm in width. The entire fruiting structure is 40 to 45 mm in length. The color of the immature fruit is Green 143A, maturing through Yellow-Green 14A, Greyed-Orange 163A, Greyed-Orange N163A, Greyed-Orange 172A to Greyed-Purple 183A. The fruit persists for four to five months.

Seed

The seed, about 200 per fruit, are mostly rounded in shape, three mm in diameter, and in color are Orange N25C in the center with Orange-Red N30C around it with Orange-Red N34A at the outermost edge.

Other than minor white fly infestation, there has been no significant disease or pest problems under the cultural conditions used.

What is claimed is:

1. A new and distinct variety of *Gardenia* plant named 'MADGA I', substantially as herein described and illustrated.

* * * * *